United States Patent
Post et al.

[11] Patent Number: 6,021,777
[45] Date of Patent: Feb. 8, 2000

[54] PORTABLE ANESTHESIA MACHINE

[75] Inventors: Terry M. Post, St. Ann; Douglas S. Pernikoff, Ballwin, both of Mo.

[73] Assignee: Anesta-Pac, Inc., Chesterfield, Mo.

[21] Appl. No.: 08/816,087

[22] Filed: Mar. 13, 1997

[51] Int. Cl.⁷ .................................................. A61M 16/00
[52] U.S. Cl. ............................... 128/204.13; 128/203.12; 128/204.14
[58] Field of Search ................ 128/203.12, 204.13, 128/204.14, 280.21, 203.26, 203.13, 203.25, 200.11

[56] References Cited

U.S. PATENT DOCUMENTS

| | | | |
|---|---|---|---|
| 3,420,232 | 1/1969 | Bickford | 128/204.13 |
| 3,438,372 | 4/1969 | Sugg et al. | 128/204.13 |
| 3,687,137 | 8/1972 | Johnson . | |
| 3,838,687 | 10/1974 | Mosher . | |
| 3,851,645 | 12/1974 | Connel . | |
| 4,444,182 | 4/1984 | Gregory | 128/204.13 |
| 4,693,853 | 9/1987 | Falb et al. . | |
| 4,879,997 | 11/1989 | Bickford | 128/200.21 |
| 4,919,125 | 4/1990 | Heaton et al. | 128/203.12 |
| 5,144,991 | 9/1992 | Wallroth et al. | 141/192 |
| 5,490,500 | 2/1996 | Reichert et al. | 128/204.13 |

FOREIGN PATENT DOCUMENTS

| | | | |
|---|---|---|---|
| 2217609 | 11/1989 | United Kingdom | 128/203.26 |

*Primary Examiner*—John G. Weiss
*Assistant Examiner*—V. Srivastava
*Attorney, Agent, or Firm*—Howell & Haferkamp, LC

[57] ABSTRACT

A portable anesthesia machine includes a vaporizer having a combinant chamber for containing a liquid anesthetic agent and a pair of diluent stems extending therein for delivering a carrier gas thereinto and providing a vaporized anesthesia agent therefrom, with a generally arcuately shaped, slotted, baffle covering an orifice in each of the diluent stems and a cotton wick extending along the height of each of a pair of carrier stems. A calibrated knob and piston/cylinder assembly controls flow of carrier gas and diluent gas into and out of the combinant chamber. A flow control manifold allows the connection of a multiple number of carrier gases and calibrated flow of any selected carrier gas into the vaporizer. A well fill port provides a convenient point for filling or draining the combinant chamber.

15 Claims, 8 Drawing Sheets

PORTABLE ANESTHESIA MACHINE

BACKGROUND AND SUMMARY OF THE INVENTION

Anesthesia machines are well known in the art and used to anesthetize humans as well as other animals most often for surgical purposes. Virtually all prior art anesthetic machines are intended to be fixedly mounted in a stable environment. This is usually required by the design of the machine and especially the vaporizer wherein the liquid anesthetic agent is contained. Should the anesthetic machine be jostled, or its attitude be changed such as by tilting or the like, control of the rate of evaporation of the liquid anesthetic is affected and, in extreme cases of tilting or inversion, liquid agent may be directly introduced into the various passageways such that the patient could be directly exposed to dangerous levels of agent. Such a circumstance would result in disastrous consequences.

Examples of prior art anesthetic machines and vaporizers may be found in U.S. Pat. Nos. 5,144,991; 4,879,997; 4,693,853; 3,687,137; 3,851,645; and U.S. Pat. No. 3,838,687. Of these, U.S. Pat. No. 3,838,687 discloses a wheeled table with an anesthetic apparatus slidably suspended below the tabletop such that it might be transported with the table as the patient on the table is moved. However, its fixed orientation prevents it from being tilted to any great extent and its construction is not directed to withstanding severe changes in its physical attitude. Other prior art devices presently commercially available suggest that they are attitude insensitive. However, in one device its construction utilizes open passageways which would readily permit the flow of liquid anesthetic agent therethrough and to the patient and hence is dangerously unacceptable. In another commercial device, a baffled wick assembly is utilized by being submersed in a generally cylindrical vaporizer chamber such that it would take 24–48 hours to clear the wick for any other liquid anesthetic agent to be used and, furthermore, it is believed that excessive tilting, jostling, or inversion of the vaporizer would tend to saturate significantly greater sections of the baffled wick such that performance would move out of clinically safe tolerance levels and present undue risk to the patient.

In order to solve these and other problems of the prior art, the inventors herein have succeeded in designing and developing an attitude insensitive anesthesia machine which is transportable, useable with any one of four industry standard liquid anesthetic agents, has a calibrated flow control manifold for the use of multiple carrier gases including a flush bypass for delivery of oxygen bursts, and which includes at its heart an improved vaporizer design having a combinant chamber with a pair of diluent stems having orifices which remain above the level of liquid anesthetic agent despite the physical orientation thereof. A baffle which is arcuately shaped and generally concentric with each diluent stem is mounted thereto and covers the orifice to divert the vapor flow into a circuitous path. Additionally, a thin cotton wick is mounted to and extends vertically along the height of each of two carrier stems. All of these features, and others, combine to provide a portable anesthesia machine which may be readily transported, used in virtually any physical attitude, is elegantly simple in design and correspondingly inexpensive, and which is ruggedized for field use under hostile environmental conditions.

More particularly, an important element of the present invention includes the vaporizer design itself which incorporates a combinant chamber wherein the liquid anesthetic agent resides upon the vaporizer being charged. A pair of generally cylindrical diluent stems extend in generally parallel fashion into the interior of the combinant chamber with each stem having an orifice located near its end and with the orifices generally facing each other and near the center of the combinant chamber such that the liquid anesthetic agent does not pour into the orifices no matter what orientation or physical attitude the vaporizer is placed in. Additionally, a generally cylindrical baffle is mounted to each diluent stem proximate the orifice with a slotted opening in the baffle on the opposite side of the diluent stem to thereby force vapor traveling between the orifices to traverse a circuitous path. With this arrangement, even though the orifices directly face each other, the carrier gas must traverse a substantial portion of the interior of the combinant chamber which leads to an effective mixing with vapor from the anesthetic agent. Thus, this arrangement permits the orifices to be physically oriented in their central location so as to accommodate jostling, tilting, and movement of the device without affecting operation. A thin cotton wick is mounted to each of the carrier stems to further aid in mixing of the carrier gas and anesthetic. As the wicks become saturated through contact with the liquid agent, it normalizes the rate of evaporation for the liquid agent to also normalize the delivery of anesthesia to the patient. The flow of carrier gas into the combinant chamber is controlled through a novel calibrated knob assembly which includes a pair of pistons and cylinders associated with the diluent stems, an actuator plate, and a roller bearing and helical ramp which moves the pistons within the cylinders in tandem to open and close the inlets to the diluent stems and also divert carrier gas between the anterior chamber and the combinant chamber. The pistons may also be advanced within the cylinders to entirely close off the diluent stems to permit the vaporizer to be transported while charged.

Liquid anesthetic agent is charged into and discharged from the combinant chamber through a well fill port. This meets various federal safety guidelines and also provides an ease of use and operability for the vaporizer unavailable in the prior art.

A multi-port flow control manifold provides still a further novel feature of the present invention as multiple carrier gases may be readily connected to the manifold and flow of any one or more of the carrier gases may be controlled and adjusted under calibration through the flow control manifold. The flow control manifold also provides a bypass flush line for delivering a flushing burst of oxygen to the patient.

While the principal advantages and features of the present invention have been explained above, a greater understanding of the invention may be obtained through reference to the drawings and detailed description which follow.

BRIEF DESCRIPTION OF THE DRAWINGS

FIGS. 7(a) and 8(b) are a perspective view and a bottom view of the superior chamber illustrating the orifice baffle and cotton wick placement;

DETAILED DESCRIPTION OF THE PREFERRED EMBODIMENT

Figure 1:
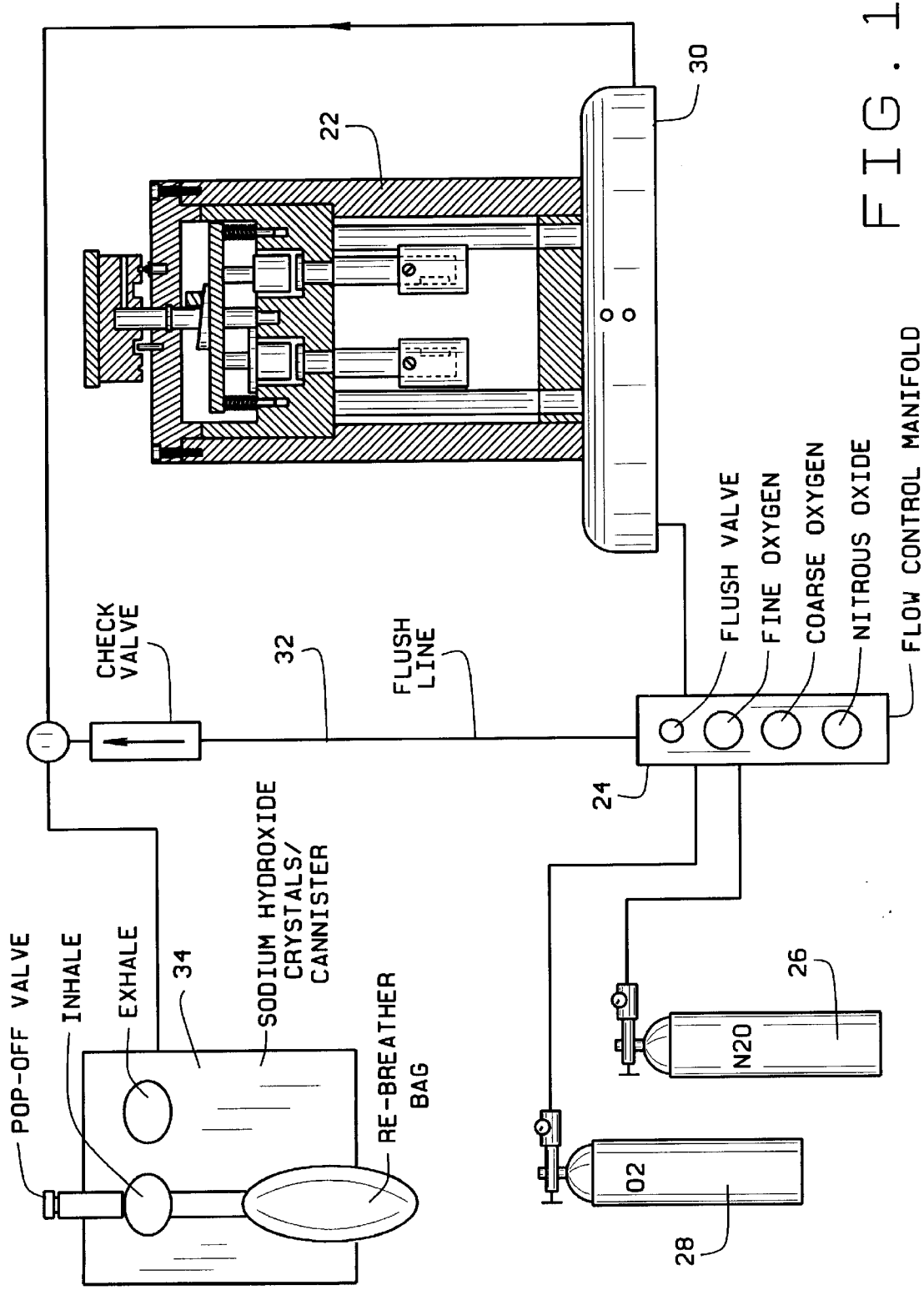
FIG. 1 is a schematic diagram of the anesthesia machine of the present invention.
Figure 2:
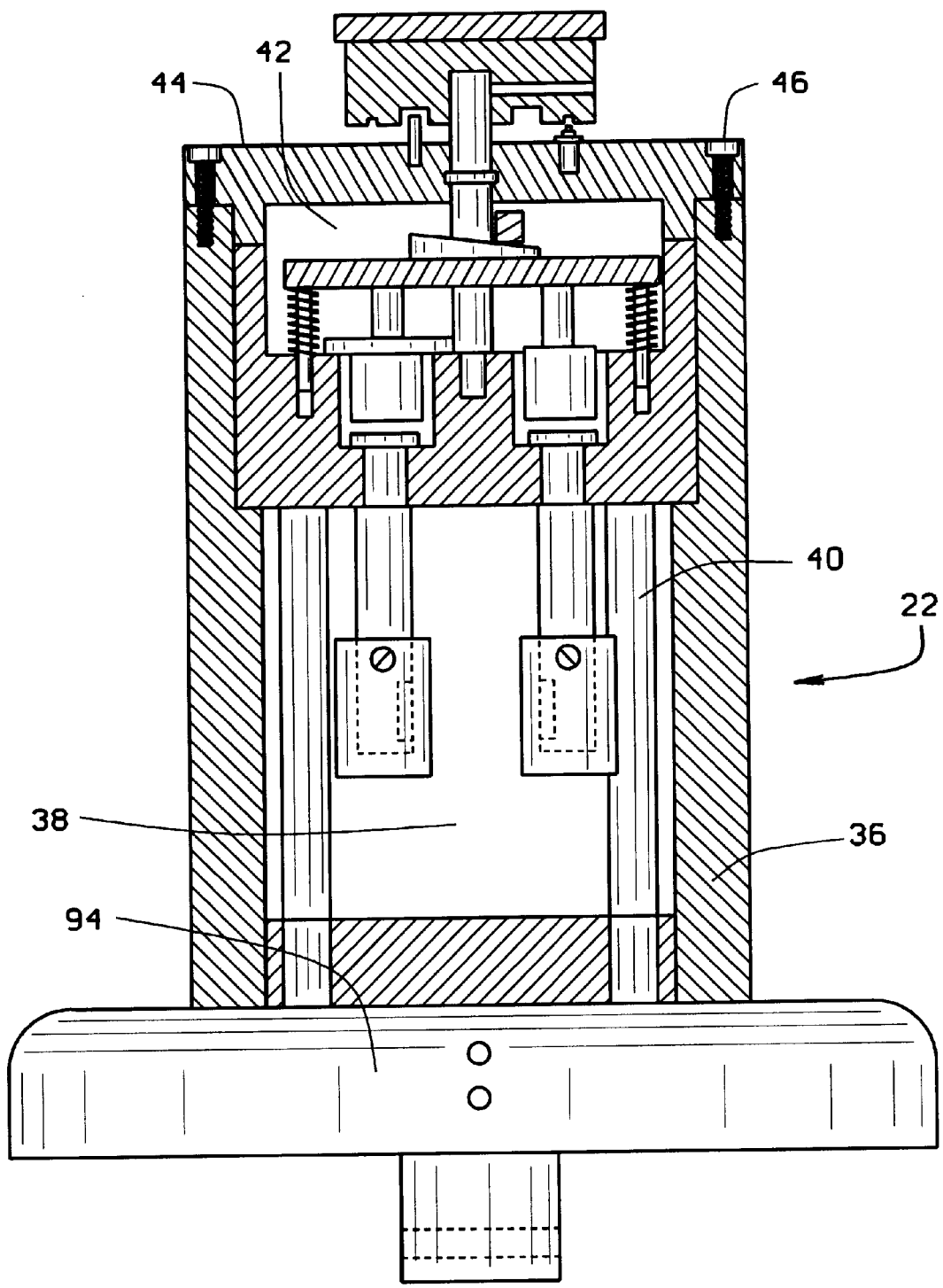
FIG. 2 is a cross-sectional view of the vaporizer detailing the combinant chamber and calibrated knob with piston and cylinder actuators.

As shown in FIG. 1, the major components of the anesthesia machine 20 of the present invention comprise a vaporizer 22, a flow control manifold 24 connected to one or more sources of carrier gas such as nitrous oxide 26 or pure oxygen 28, a well fill port 98 through which liquid anesthetic agent is charged into or discharged from the vaporizer 22, a bypass flush line 32 for bypassing vaporizer 22 with a flush of pure oxygen to the patient, and a sodium hypochlorite cannister 34 for removing $CO_2$ from the breathing circuit. As shown in FIG. 2, the vaporizer 22 is generally comprised of a cylindrical body 36 in which is formed a generally rectangular combinant chamber 38. At the uppermost portion of the body 36 there is formed a superior chamber 42 by manifold cap 44 held in place by screws 46.

Figure 3:
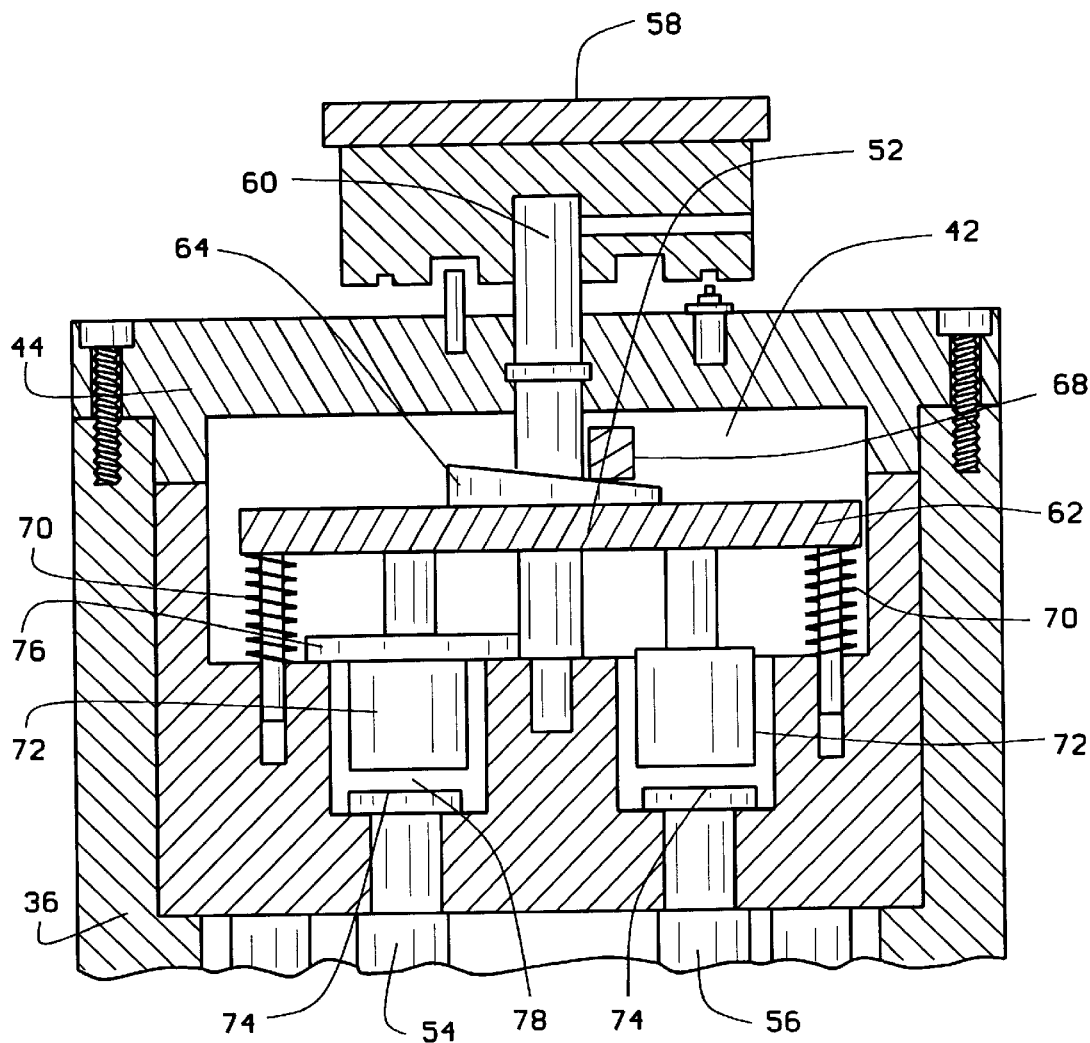
FIG. 3 is an enlarged cross-sectional view of the calibrated knob with its associated dual pistons and cylinders with actuator assembly.
Figure 4:
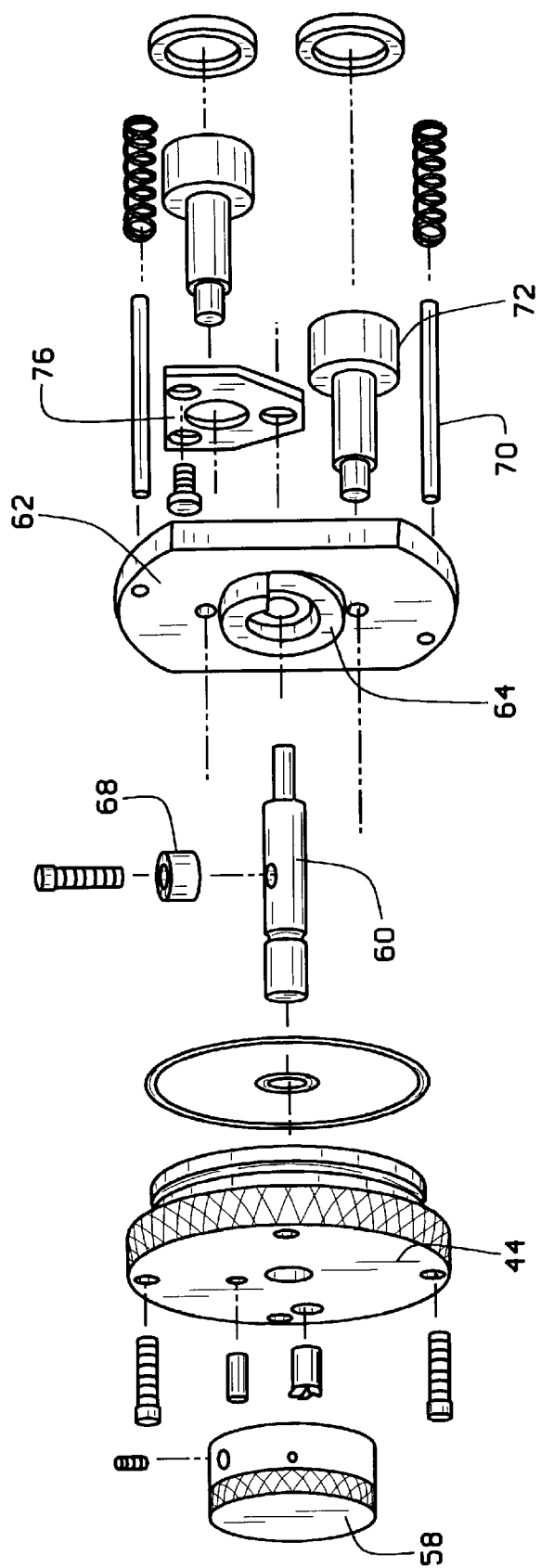
FIG. 4 is an exploded view of the calibrated knob with dual pistons and cylinders actuator assembly.
Figure 5:
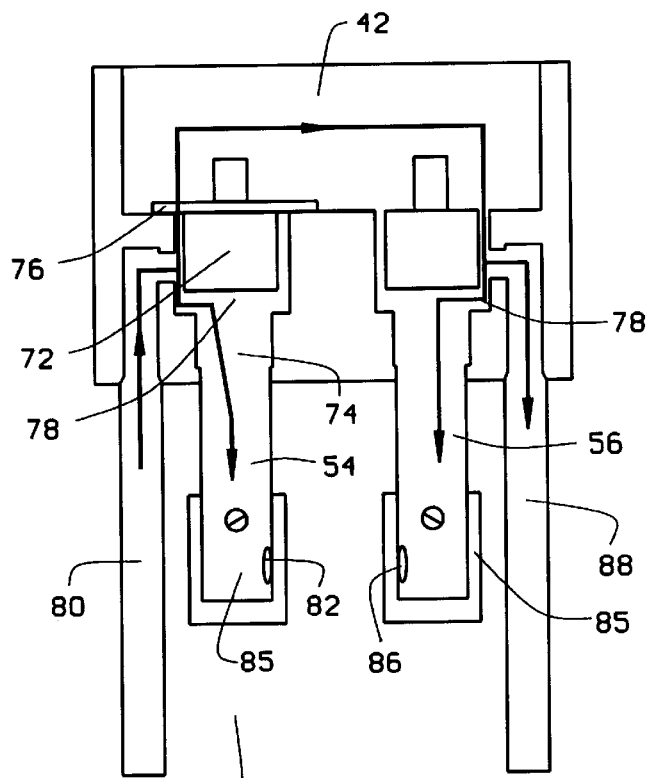
FIG. 5 is a diagrammatic view detailing the carrier gas and diluent gas pathways through the vaporizer.
Figure 6:
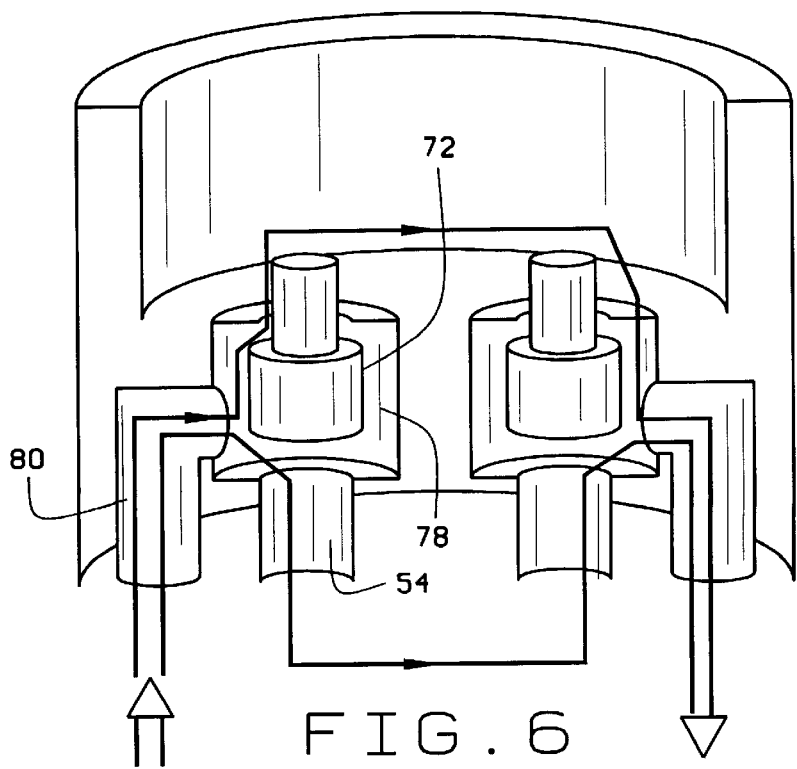
FIG. 6 is a diagrammatic view further detailing the flow of carrier gas and diluent gas through the anterior chamber.

As shown in FIGS. 3 and 4, a calibrated knob and piston/cylinder actuator assembly 52 is used to control the flow of carrier gas through the superior chamber 42 and into and out of the combinant chamber 38 by way of diluent stems 54, 56. The calibrated knob assembly 52 includes a calibrated knob 58 connected to an actuating stem 60 which rests against an actuator plate 62. A helical ramp 64 and roller bearing assembly 68 deflect the actuator plate 62 against a pair of spring-loaded guide pins 70 to correspondingly move pistons 72 closer to or further away from inlets 74 of diluent stems 54, 56. A cover plate 76 covers the top of inlet cylinder 78 so that as piston 72 is withdrawn against it, the flow of carrier gas is prohibited into superior chamber 42 and deflected down through inlet 74 and diluent stem 54 into combinant chamber 38. The flow of carrier gas and diluent gas is shown in schematic detail in FIGS. 5 and 6. As shown therein, the carrier gas enters through the ascending carrier stem 80 and into cylinder 78 where it is diverted by piston 72 either upwardly into superior chamber 42 or downwardly into the inlet 74 of the descending diluent stem 54 and through orifice 82 into combinant chamber 38. Within combinant chamber 38, the carrier gas mixes with the evaporating liquid anesthetic agent to form the appropriate gaseous mixture which exits through orifice 86 in ascending diluent stem 56. As shown in FIG. 4, a pair of baffles 84, 85 are mounted to the diluent stems 54, 56 and serve to divert the flow of vapor exiting orifice 82 in diluent stem 54 and entering orifice 86 in diluent stem 56. This is explained in greater detail, infra. Upon entering ascending diluent stem 56, the gaseous mixture flows upwardly into cylinder 78 where it may be further mixed with more carrier gas from superior chamber 42. This gaseous mixture then proceeds out of cylinder 78 and into the descending carrier stem 88 and onto the patient. As would be apparent upon review of the flow of gas and the location of the liquid agent, advancing the calibration knob to its extreme will bring pistons 72 into sealing contact with inlets 74 of diluent stems 54, 56 to thereby seal the vapors and liquid anesthetic agent within combinant chamber 38. In this orientation, the anesthesia device 20 may be transported without fear of contamination or migration of the liquid anesthetic agent to undesirable areas of the vaporizer 22 which would hamper its calibration and delay its subsequent reuse. In this orientation, liquid anesthetic agent is prevented from entering cylinder 78 and superior chamber 42 as well as carrier stems 80, 88, all of which will be kept free from liquid anesthetic agent and undesirable and uncontrollable anesthetic effects upon the patient. Should calibration knob 58 be advanced to its other extreme, piston 72 advances upwardly to rest against cover plate 76. This forces all of the carrier gas down into the inlet 74 of descending diluent stem 54 and out through orifice 82 into combinant chamber 38. This position provides maximum delivery of anesthetic agent in concentration through the vaporizer 22.

Figure 7A:
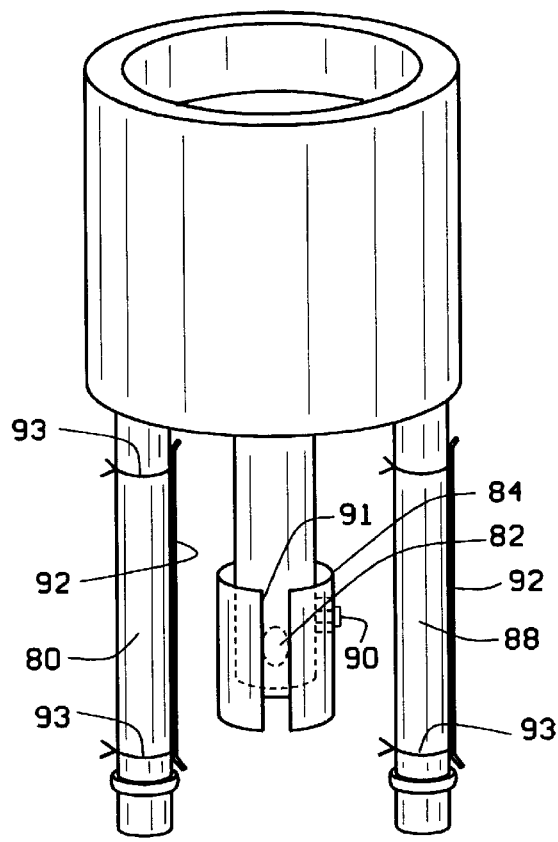
Figure 7B:
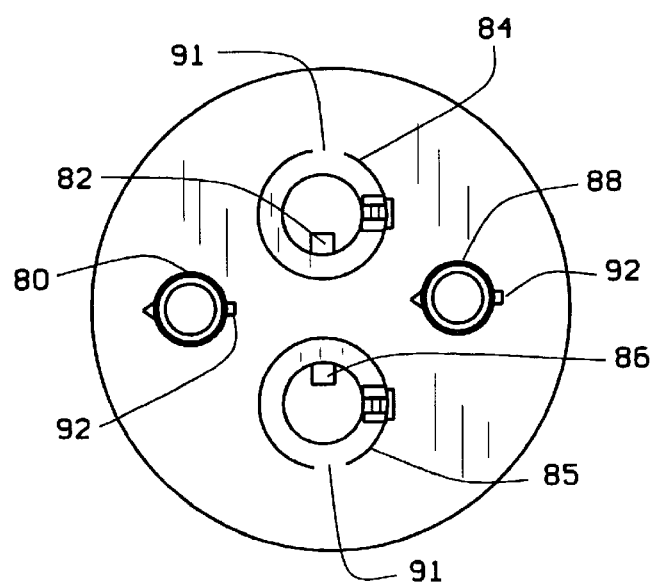
Figure 12:
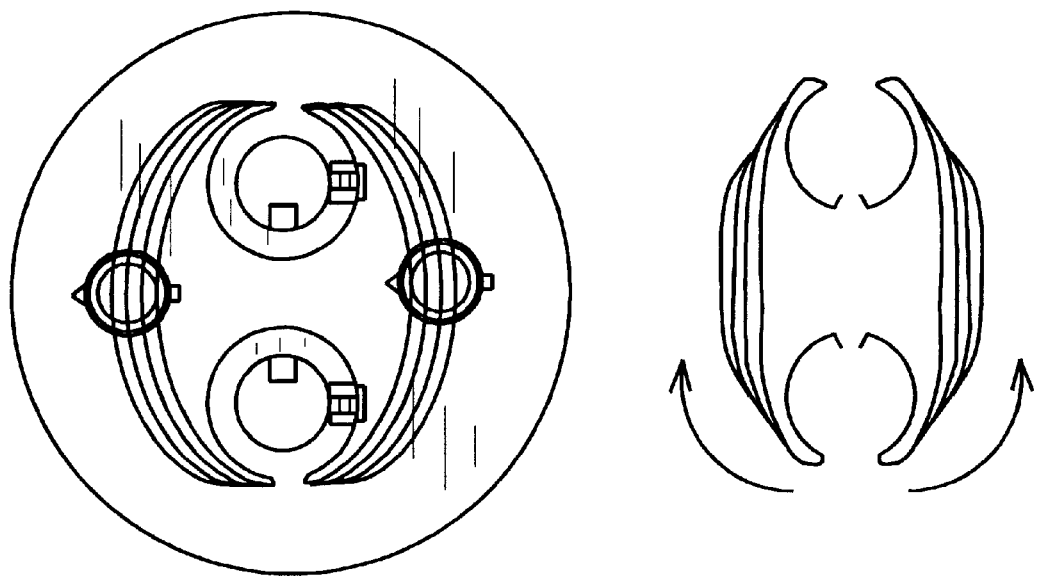
FIG. 12 is a schematic view of the expected vapor flow pattern between orifices.

As shown in FIGS. 7(a) and (b), each baffle 84, 85 is cylindrical in shape and sized to be of a height which allows the entire orifice in each corresponding diluent stem to be substantially covered thereby, while being held in a spaced-apart relationship by a screw and spacer 90. Each baffle 84, 85 has a slot 91 which extends the height of each baffle 84, 85 and provides a pathway, along with the spacing between the baffle 84, 85 and its corresponding diluent stem 54, 56 for vapor to flow into and out of its corresponding orifice, as appropriate. As is particularly noted in FIG. 7(b), baffles 84, 85 divert the flow of vapor between the orifices such that, even though the orifices are directly aligned with each other and facing each other, vapor must flow in a circuitous, extended path length, and traverse combinant chamber thereby mixing with vapor from liquid anesthetic agent prior to exiting combinant chamber 38 through the other orifice. The vapor flow path is shown more particularly in FIG. 12. Thus, with this arrangement, orifices 82, 86 may be directly aligned and centrally located within combinant chamber 38 and yet provide a significant mixing of carrier gas with anesthetic agent. To further aid in this mixing, a pair of cotton wicks 92 each of which comprise approximately a three inch strip of one-eighth inch thick one hundred percent cotton are mounted to carrier stems 80, 88 with twisted copper wire 93 at the top and bottom thereof. In operation, these cotton wicks become saturated with liquid anesthetic agent and also serve to mix the carrier gas and anesthetic agent effectively as the carrier gas traverses the combinant chamber 38 between orifices 82, 86.

Figure 8:
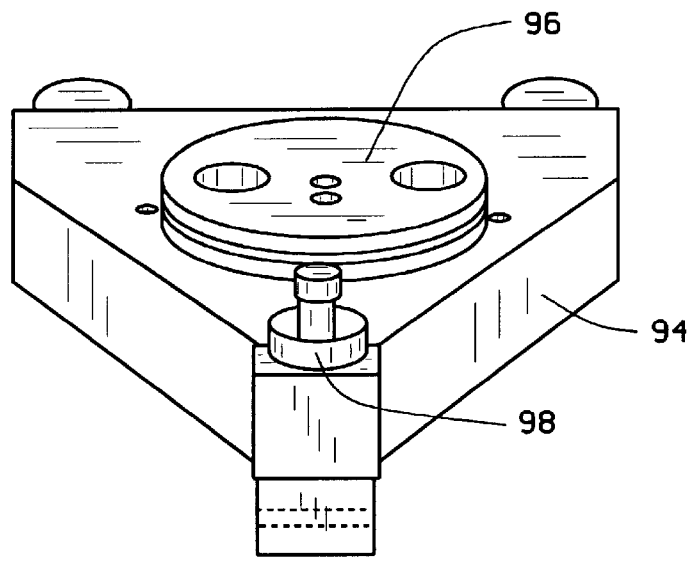
FIG. 8 is a perspective view of the base.
Figure 9:
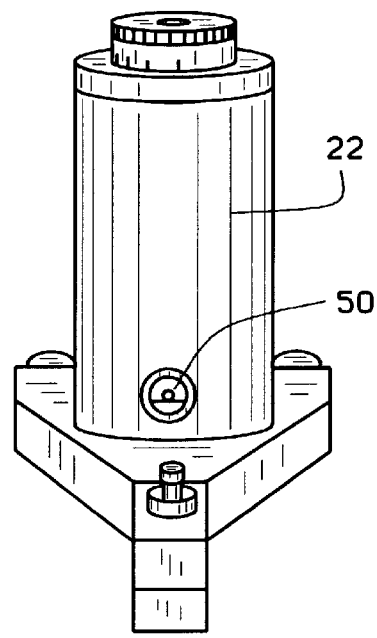
FIG. 9 is a perspective view of the vaporizer with base assembled.
Figure 11:
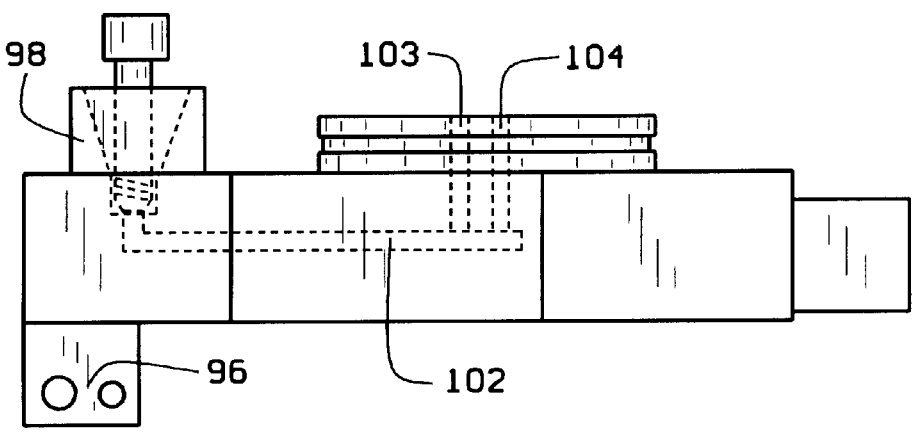
FIG. 11 is a side view of the fill conduit of the base.

As shown in FIGS. 8 and 9, a well fill port 98 includes a base plate 94 and mounting ring 96 for mounting the vaporizer assembly 22. The well fill port 98 includes a well fill conduit 96 which is detailed in FIG. 11. As shown therein, a well fill port 98 will accommodate 100 ml of IsoFlurane™ liquid anesthetic, as known to those of ordinary skill in the art. The fill port conduit 98 includes a spring-loaded pull pin 100 to control the filling and draining of liquid anesthetic agents from the vaporizer 22 through an internal conduit 102 which is doubly ported into the combinant chamber 38 of vaporizer 22 through ports 103, 104.

Figure 10:
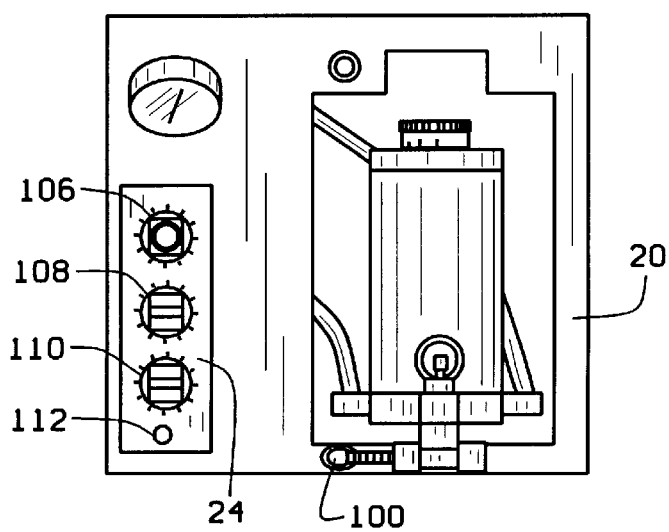
FIG. 10 is a top view of the portable anesthesia device of the present invention detailing the intake manifold.

As shown in FIG. 10, the flow control manifold 24 has a plurality of ported entries controlled by a calibrated knob and piston assembly 106, 108, and 110 through which carrier gas may be connected for delivery to manifold 22, as explained above. A flush valve 112 is also provided in manifold 24 to permit the manifold 22 to be bypassed and for the patient to receive a flush of a burst of an oxygen gas, as preselected in flow control manifold 24.

There are various changes and modifications which may be made to the invention as would be apparent to those skilled in the art. However, these changes or modifications are included in the teaching of the disclosure and it is intended that the invention be limited only by the scope of the claims appended hereto.

What is claimed is:

1. An attitude insensitive anesthesia machine comprising a vaporizer, the vaporizer including a combinant chamber for containing a charge of a liquid anesthetic agent, a pair of diluent stems extending into said combinant chamber, each of said diluent stems being substantially cylindrically shaped, and extending to a point substantially near the center of the chamber, one of said diluent stems carrying a carrier gas into the chamber and the other of said diluent stems carrying a diluent gas out of the chamber, each of said stems having an orifice through which vapor passes directly into or out of the combinant chamber, each of said orifices facing each other, and spaced from each stem end, said orifices being located within said chamber and adapted to lie above the surface level of the agent regardless of the physical attitude of the vaporizer, and a baffle surrounding each of said diluent stems, each of said baffles being spaced apart from and generally concentric with said stems at the location of said orifices to thereby direct the flow of gas around said stems.

2. The anesthesia machine of claim 1 further comprising a wick mounted to each of a pair of carrier stems.

3. The anesthesia machine of claim 2 wherein each of said wicks comprise a cotton strip extending along a substantial portion of the length of each of said carrier stems.

4. The anesthesia machine of claim 3 wherein the vaporizer further comprises a calibration knob assembly to adjust the flow of the carrier gas into the combinant chamber.

5. The anesthesia machine of claim 4 wherein the knob assembly includes a roller bearing riding atop a ramp attached to a twist knob, the ramp being affixed to an actuator plate, and the actuator plate being secured to a pair of pistons, each of said pistons being positioned with respect to each of said diluent stems so that as said twist knob is turned, the ramp is moved with respect to the roller bearing to thereby advance or withdraw the actuator plate and pistons with respect to an inlet for each of said diluent stems.

6. The anesthesia machine of claim 5 further comprising a cover plate associated with one of the diluent stems and piston so that said piston may be withdrawn away from its associated inlet and adjacent said cover plate to thereby divert substantially all of said carrier gas into one of the diluent stems.

7. The anesthesia machine of claim 6 wherein each of said pistons is located in an associated cylinder, and wherein the carrier stems comprise an ascending carrier stem communicating with the cylinder associated with a descending diluent stem and through which carrier gas is input to said vaporizer, and a descending carrier stem communicating with the cylinder associated with an ascending diluent stem and through which diluent gas exits said vaporizer.

8. The anesthesia machine of claim 7 further comprising a manifold communicating with the ascending carrier stem, said manifold having a plurality of graduated connections for input of one of a plurality of different carrier gases.

9. The anesthesia machine of claim 8 wherein the vaporizer further comprises a well fill port.

10. An attitude insensitive anesthesia machine comprising a vaporizer, the vaporizer including a combinant chamber for containing a liquid anesthetic agent, a pair of diluent stems extending into said combinant chamber, each of said stems having an inlet at its top, and an orifice near its bottom, said orifices permitting gas to pass through said combinant chamber and between said stems, and a calibrated knob and piston assembly for controlling the flow of a carrier gas into and out of said combinant chamber to thereby control the rate of delivery of the liquid agent by the machine, said calibrated knob and piston assembly including a piston and cylinder associated with each diluent stem, and an actuator for moving the pistons in response to a moving of the calibrated knob between a bypass position where the pistons substantially seal an inlet to each of the diluent stems, and a maximum position where one of the pistons substantially seals an alternate route for a carrier gas around said combinant chamber.

11. The attitude insensitive anesthesia machine of claim 10 further comprising a manifold in fluid communication with one of said cylinders, said manifold having a plurality of intake ports adapted for the connection of a plurality of sources of a carrier gas.

12. The attitude insensitive anesthesia machine of claim 11 further comprising a baffle surrounding each of said diluent stems and its associated orifice, said baffles being fixedly secured to said stems and being arcuate in shape and aligned over said orifices to thereby direct the flow of gas around said stems when traveling either into or out of said orifices.

13. The attitude insensitive anesthesia machine of claim 12 further comprising a fill port communicating with the combinant chamber and through which a selected anesthetic agent may be passed to charge or discharge the vaporizer.

14. An attitude insensitive anesthesia machine comprising a vaporizer, the vaporizer including a combinant chamber for containing a charge of a liquid anesthetic agent, a pair of diluent stems extending into said combinant chamber for introducing said anesthetic agent into said chamber, each of said stems having an orifice through which vapor may pass, a baffle surrounding each of said orifices, each of said baffles being oriented to force gas flow between said orifices into an extended path length, and a cotton wick extending vertically along the height of each of a pair of carrier stems.

15. The attitude insensitive anesthesia machine of claim 14 wherein each of said baffles has a vertical slot therein oriented on the opposite side of its corresponding diluent stem as includes the orifice.

\* \* \* \* \*